(12) United States Patent
Yamamoto et al.

(10) Patent No.: US 8,580,557 B2
(45) Date of Patent: Nov. 12, 2013

(54) CASEIN HYDROLYZATE, PROCESS FOR PRODUCING THE SAME AND USE THEREOF

(75) Inventors: Naoyuki Yamamoto, Sagamihara (JP); Seiichi Mizuno, Machida (JP); Shingo Nishimura, Sagamihara (JP); Hideo Nishimura, legal representative, Yosa-gun (JP); Takanobu Gotou, Machida (JP); Keiichi Matsuura, Mitaka (JP); Tadashi Shinoda, Sagamihara (JP)

(73) Assignee: Calpis Co., Ltd., Tokyo (JP)

( * ) Notice: Subject to any disclaimer, the term of this patent is extended or adjusted under 35 U.S.C. 154(b) by 125 days.

(21) Appl. No.: 12/873,500

(22) Filed: Sep. 1, 2010

(65) Prior Publication Data

US 2011/0082281 A1 Apr. 7, 2011

Related U.S. Application Data (63) Continuation of application No. 10/565,497, filed as application No. PCT/JP2004/010928 on Jul. 30, 2004, now abandoned.

(30) Foreign Application Priority Data

Aug. 1, 2003 (JP) ................................. 2003-285007

(51) Int. Cl.
| | |
|---|---|
| *C12N 1/00* | (2006.01) |
| *C12N 9/62* | (2006.01) |
| *A61K 38/00* | (2006.01) |
| *A61K 38/05* | (2006.01) |
| *A61K 38/06* | (2006.01) |
| *C12N 9/50* | (2006.01) |
| *C12N 9/48* | (2006.01) |
| *A61K 47/00* | (2006.01) |
| *A61K 38/55* | (2006.01) |
| *A23C 9/12* | (2006.01) |
| *C12P 21/06* | (2006.01) |
| *A61P 9/12* | (2006.01) |

(52) U.S. Cl.
USPC ....... 435/256.1; 435/68.1; 435/212; 435/219; 435/225; 424/439; 426/34; 514/15.7; 514/16.2; 514/16.3; 514/21.91; 530/316; 530/331; 530/343; 530/344

(58) Field of Classification Search
None
See application file for complete search history.

(56) References Cited

U.S. PATENT DOCUMENTS 5,314,873 A * 5/1994 Tomita et al. ................. 514/18.8

FOREIGN PATENT DOCUMENTS

| JP | 59044324 | 3/1984 |
|---|---|---|
| JP | 63258599 | 10/1988 |
| JP | 2039896 | 2/1990 |
| JP | 05-015314 | 1/1993 |
| JP | 05-252979 | 10/1993 |
| JP | 06-128287 | 5/1994 |
| JP | 10212245 | 8/1998 |
| JP | 2001-136995 | 5/2001 |
| JP | 2001278893 | 10/2001 |
| JP | 2003-024012 | 1/2003 |
| JP | 2003-210138 | 7/2003 |
| WO | 94/25580 | 11/1994 |
| WO | 98/51803 | 11/1998 |
| WO | WO0139613 A1 | 6/2001 |
| WO | 03/044044 | 5/2003 |

OTHER PUBLICATIONS

Greenberg, R., et al "Human-Casein: Amino Acid Identification of Phosphorylation Sites" The Journal of Biological Chemistry. 1984, 259(8), 5132-5138.*

Lehtinen R, Jauhiainen T, Kankuri E, Lindstedt K, Kovanen PT, Kerojoki O, Korpela R, Vapaatalo H. "Effects of Milk Casein-derived Tripeptides Ile-Pro-Pro, Val-Pro-Pro, and Leu-Pro-Pro on Enzymes Processing Vasoactive Precursors in vitro." Arzneimittelforschung (Drug Research). 2010;60(4):182-5 (PubMed Abstract only).*

Sipola, M; Finckenberg, P; Santisteban, J; Korpela, R; Vapaatalo, H; Nurminen, M-L "Long-Term Intake of Milk Peptides Attenuates Development of Hypertension in Spontaneously Hypertensive Rats" J Physiol Pharm, 2001, 52(4),pp. 745-754.*

Tony Byun, et al., Synergistic Action of an X-Prolyl Dipeptidyl Aminopeptidase and a Non-Specific Aminopeptidase in Protein Hydrolysis, Journal of Agricultural and Food Chemistry, American Chemical Society, vol. 49, No. 4, 2001, pp. 2061-2063.

Hiroki Tatsumi, et al., Cloning and Expression in Yeast of a cDNA Clone Encoding *Aspergillus oryzae* Neutral Protease II, a Unique Metalloprotease, Molecular and General Genetics, vol. 228, 1991, pp. 97-103.

Rosina Lopez-Fandino, et al., Proteolytic Activity of Two Commercial Proteinases from *Aspergillus oryzae* and *Bacillus subtilis* on Ovine and Bovine Caseins, Journal of Dairy Research, vol. 58, 1991, pp. 461-467.

(Continued)

*Primary Examiner* — Chris R Tate
*Assistant Examiner* — Aaron J Kosar
(74) *Attorney, Agent, or Firm* — Fish & Richardson P.C.

(57) ABSTRACT

The present invention relates to a casein hydrolysate containing free amino acids and in vivo indigestible peptides having minimally suppressed in vivo enzymatic digestibility, and expected to express functions, such as hypotensive effect, in living organism, and to a method for preparing such a hydrolysate, and use thereof. The casein hydrolysate of the present invention contains free amino acids and peptides, such as in vivo indigestible peptides including Xaa-Pro and Xaa-Pro-Pro, obtained by hydrolyzing animal milk casein to have an average chain length of not longer than 2.1 in terms of the number of amino acid residues, and has ACE inhibitory activity or hypotensive effect.

14 Claims, 5 Drawing Sheets

(56) References Cited

OTHER PUBLICATIONS

Yasunori Nakamura, et al., Antihypertensive Effect of Sour Milk and Peptides Isolated from It That are Inhibitors to Angiotensin I-Converting Enzyme, Journal of Dairy Science, American Dairy Science Association, vol. 78, No. 6, 1995, pp. 1253-1257.

Yasunori Nakamura, et al., Purification and Characterization of Angiotensin I-Converting Enzyme Inhibitors from Sour Milk, Journal of Dairy Science, vol. 78, Apr. 1995, pp. 777-783.

N. Yamamoto, et al., Antihypertensive Peptides Derived from Milk Proteins, Nahrung—Food, vol. 43, No. 3, 1999, pp. 159-164.

Alexander M. Blinkovsky, et al., A Non-Specific Aminopeptidase From *Aspergillus*, Biochimica et Biophysica ACTA, vol. 1480, Jul. 14, 2000, pp. 171-181.

Yoshitsugu Iemura, et al., Properties of the Peptides Liberated from Rice Protein in Sokujo-moto, Journal of Bioscience and Bioengineering, vol. 88, No. 3, 1999, pp. 276-280.

Myeong-Rak Choi, et al., Effective Digestion of Casein with Agar Gel-Entrapped Cell Wall Fraction-Bound Enzymes of *Aspergillus oryzae* as Immobilized Proteases, Journal of Fermentation and Bioengineering, vol. 72, No. 5, 1991, pp. 379-383.

Naoyuki Yamamoto et al., Antihypertensive Effect of the Peptides Derived from Casein by an Extracellular Proteinase from *Lactobacillus helveticus* CP790, Journal of Dairy Science, 77:917-922 (1994).

Byun, T., et al., "Synergistic Action of an X-Prolyl Dipeptidyl Aminopeptidase and a Non-Specific Aminopeptidase in Protein Hydrolysis" J. Agic. Food Chem., 49(4), pp. 2061-2063 (2001).

Tachi, et al., "An X-Prolyl Dipeptidyl-Aminopeptidase From *Aspergillus oryzae*," Phytochemistry 31(11):3707-3709, 1992.

\* cited by examiner

CASEIN HYDROLYZATE, PROCESS FOR PRODUCING THE SAME AND USE THEREOF

CROSS REFERENCE TO PRIOR APPLICATIONS

This is a continuation of U.S. Ser. No. 10/565,497, filed Sep. 12, 2006, which is the U.S. National Phase application under 35 U.S.C. §371 of International Patent Application No. PCT/JP2004/010928 filed on Jul. 30, 2004, and claims the priority of Japanese Patent Application No. JP2003-285007, filed Aug. 1, 2003, all of which are incorporated by reference herein. The International Application was published in Japanese on Feb. 10, 2005 as WO 2005/012542 A1 under PCT Article 21(2).

FIELD OF ART

The present invention relates to casein hydrolysate which is obtained by hydrolysis of animal milk casein, is expected to exhibit various functions including angiotensin converting enzyme inhibitory activity and hypotensive effect, and is useful for various food and medicine, as well as to a method for preparing such casein hydrolysate, and use thereof.

BACKGROUND ART

A variety of peptides have been reported having various functions, such as hypotensive effect, anti-bacterial activity, calcium solubilizing effect, and immunomodulating effect, and these peptides are in use in food and medicine.

For example, hypotensive peptides have been proposed, many of which have angiotensin converting enzyme (abbreviated as ACE hereinbelow) inhibitory activity. ACE converts a precursor, angiotensin I, to angiotensin II having vasoconstrictive activity in living organism, to thereby raise the blood pressure. Thus peptides having ACE inhibitory activity are expected to exhibit hypotensive effect by inhibiting ACE to suppress production of angiotensin II in living organism. In the development of hypotensive peptides, researches are usually directed first to peptides having ACE inhibitory activity, so that hypotensive effect of the proposed peptides are mainly indicated by ACE inhibitory effect as reference index. A great number of agents having hypotensive effect evaluated by the ACE inhibitory activity as reference index, have been proposed to date, and are in use for prevention and treatment of hypertension.

In production of functional peptides, such as peptides having hypotensive effect evaluated by the ACE inhibitory effect, in particular, in production of functional peptides by digestion of food protein with enzymes, complicated steps are usually required after the enzymatic digestion, such as concentration, purification, and isolation of the digested products, for improving expression of the functional effects.

As peptides that are absorbed through the alimentary canal into blood to express their functions in living organism, in vivo indigestible peptides are expected to be advantageous that have high absorbability and digestion resistance against various digestive enzymes in living organism. However, it is not known in detail which peptides contribute to enhancement of the in vivo digestion resistance. Thus development of enzymatic digestion products for food or medicine and methods for producing such products are desired, which products have high in vivo digestion resistance, and can effectively express their desired functions without undergoing complicated processes such as concentration, purification, or isolation after the enzymatic digestion.

For example, Patent Publication 1 discloses a method for producing a low molecular weight peptide mixture mainly composed of dipeptides and tripeptides, having an average chain length of not longer than 3, and having excellent intestinal absorbability. The peptide mixture is prepared from soybean protein by simultaneous or sequential action of two or more enzymes having endoprotease activity but substantially no exoprotease activity, with not higher than 5% free amino acids being generated. Patent Publication 2 discloses functional food utilizing soybean protein digestion products and method for producing the same. The digestion products contain as active ingredients a dipeptide and tripeptides consisting of Ala-Tyr, Gly-Tyr-Tyr, Ala-Asp-Phe, and Ser-Asp-Phe, prepared by digesting heat denatured soybean protein with enzymes such as proteases derived from *Aspergillus oryzae*. The digestion products preferably have an average peptide chain length of 2 to 4, and contain 20 to 30 wt % free amino acids.

However, these enzymatic digestion products of soybean protein have components that are quite different from those of enzymatic digestion products of animal milk casein. Thus the above patent publications suggest nothing about methods for preparing, from animal milk casein as a staring material, casein digestion products and casein hydrolysate that have a high concentration of active ingredients and excellent absorbability in living organism, and may be used without necessarily undergoing complicated processes such as concentration, purification, and isolation.

On the other hand, Patent Publications 3 and 4 propose methods for preparing peptides having various functions by digesting animal milk casein with enzymes such as proteases and peptidases, and particular functional peptides obtained by the methods.

The enzymatic digestion products disclosed in these publications are, however, for obtaining particular peptides as active ingredients. Thus there is no teaching in these publications as to hydrolysis of animal milk casein to have an average chain length of not longer than 2.1, specific process of the hydrolysis, and effectiveness of the casein hydrolysate having the particular average chain length.

Patent Publication 1: JP-5-252979-A
Patent Publication 2: JP-2003-210138-A
Patent Publication 3: JP-6-128287-A
Patent Publication 4: JP-2001-136995-A

SUMMARY OF THE INVENTION

It is an object of the present invention to provide a casein hydrolysate containing in vivo indigestible peptides and free amino acids having minimized in vivo enzymatic digestibility, and expected to express functions, such as hypotensive effect, in living organism.

It is another object of the present invention to provide a method for preparing the casein hydrolysate mentioned above, which allows easy and efficient production of the above casein hydrolysate without necessarily involving complicated processes.

It is yet another object of the present invention to provide an agent having ACE inhibitory activity or hypotensive effect that contains in vivo indigestible peptides and free amino acids, is expected to have excellent hypotensive effect in living organism, and is useful for various functional food or medicine.

The present inventors have made intensive researches for achieving the above objects, to find out that, by hydrolyzing animal milk casein to have an average chain length of not longer than 2.1 in terms of the number of amino acid residues, a casein hydrolysate containing free amino acids and low molecular weight peptides, such as tripeptides and dipeptides, may be obtained, wherein free amino acids and in vivo indigestible peptide molecules having a residue Pro at the carboxyl terminal are efficiently formed.

The present inventors have also found out that the in vivo indigestible peptides having a residue Pro at the carboxyl terminal are expected to have high digestion resistance against in vivo peptidases, so that it is quite possible for such indigestible peptides to fully exhibit their functions in living organism, and that the casein hydrolysate has a high content of peptides having good in vivo absorbability, such as dipeptides and tripeptides, so that the casein hydrolysate is capable of fully exhibiting various functions, such as hypotensive effect, in living organism, to thereby completing the present invention.

Further, the present inventors have made researches for enzymes that efficiently produce the casein hydrolysate of the present invention from various known enzymes to find out that a particular class of enzymes is particularly capable of efficiently producing the casein hydrolysate of the present invention.

According to the present invention, there is provided a casein hydrolysate comprising free amino acids and peptides obtained by hydrolyzing animal milk casein to have an average chain length of not longer than 2.1 in terms of the number of amino acid residues. More specifically, the present invention provides the casein hydrolysate mentioned above wherein the peptides comprises in vivo indigestible peptides consisting of dipeptides having a sequence Xaa-Pro and tripeptides having a sequence Xaa-Pro-Pro, and wherein a content of the dipeptides having a sequence Xaa-Pro is not lower than 5 wt % of a total amount of the peptides and the free amino acids in the hydrolysate, and a content of the tripeptides having a sequence Xaa-Pro-Pro is not lower than 1 wt % of a total amount of the peptides and the free amino acids in the hydrolysate. As used herein, Xaa may be any amino acid.

According to the present invention, there is also provided a method for preparing the casein hydrolysate mentioned above comprising the step of (A) hydrolyzing animal milk casein to have an average chain length of not longer than 2.1 with a group of enzymes capable of digesting animal milk casein into a casein hydrolysate having an average chain length of not longer than 2.1 in terms of the number of amino acid residues.

According to the present invention, there is also provided an agent having ACE inhibitory activity or hypotensive effect comprising the above casein hydrolysate as an active ingredient.

According to the present invention, there is further provided use of the above casein hydrolysate in the manufacture of functional food or medicine having ACE inhibitory activity or hypotensive effect.

The casein hydrolysate of the present invention contains free amino acids and low molecular weight peptides such as in vivo indigestible peptides, obtained by hydrolyzing animal milk casein to have an average chain length of not longer than 2.1 in terms of the number of amino acid residues. Thus the present casein hydrolysate is expected to exhibit, by oral administration, excellent in vivo absorbability and various functions in living organism, and to be useful for various functional food, medicine, and food additives. For example, the present casein hydrolysate is expected to be used in an agent having ACE inhibitory activity or hypotensive effect containing the present hydrolysate as an active ingredient.

The present method includes the step (A) of hydrolyzing animal milk casein to have an average chain length of not longer than 2.1 with a group of enzymes capable of digesting animal milk casein into a casein hydrolysate having an average chain length of not longer than 2.1 in terms of the number of amino acid residues. Thus, the method allows easy and efficient production of the casein hydrolysate of the present invention. Accordingly, the present method is advantageous in industrial production of the casein hydrolysate of the present invention.

PREFERRED EMBODIMENTS OF THE INVENTION

The present invention will now be explained in detail.

The casein hydrolysate of the present invention contains free amino acids and peptides obtained by hydrolyzing animal milk casein to have a particular range of average chain length in terms of the number of amino acid residues. The amount of the free amino acids and the peptides is preferably not less than 80 wt %, more preferably 80 to 90 wt % of the total amount of the casein hydrolysate. It is particularly preferred that the hydrolysate has a particular content of in vivo indigestible peptides as the peptides, composed of dipeptides having the sequence Xaa-Pro and tripeptides having the sequence Xaa-Pro-Pro. The peptides may be peptide salts.

As used herein, the average chain length may be expressed as a ratio of the total number of moles of the peptides and the free amino acids generated by hydrolysis of animal milk casein with respect to the number of moles of all the amino acids in the casein acid hydrolysate of the same weight. Here, the casein acid hydrolysate is obtained by digesting casein protein into single amino acids.

The average chain length may be determined, for example, by evaluating the molar concentrations of the amino groups in the hydrolysates by the OPA method using an OPA (o-phthalaldehyde) reagent, which colors by reaction with amino groups, and expressed as:

Average chain length=(number of moles of amino groups in casein acid hydrolysate)/(number of moles of amino groups in casein enzyme hydrolysate).

As used herein, the in vivo indigestible peptides mean dipeptides Xaa-Pro and tripeptides Xaa-Pro-Pro having Pro at the carboxyl terminal, which have high digestion resistance against in vivo peptidases when absorbed intestinally in living organism.

According to the present invention, the average chain length of the hydrolysate obtained by hydrolyzing animal milk casein is not longer than 2.1, preferably 1.1 to 2.1, more preferably 1.3 to 2.1, in terms of the number of amino acid residues. With the average chain length of longer than 2.1, the contents of the desired dipeptides and tripeptides as well as the free amino acids are low, and thus the content of the desired in vivo absorbable and in vivo indigestible peptides is low.

The content of the dipeptides having the sequence Xaa-Pro in the casein hydrolysate of the present invention is usually not lower than 5 wt %, preferably 5 to 25 wt % of the total amount of the peptides and the free amino acids in the hydrolysate. At less than 5 wt %, desired in vivo absorbability is lowered and the expression of the functions is insufficient.

The content of the tripeptides having the sequence Xaa-Pro-Pro in the casein hydrolysate of the present invention is usually not lower than 1 wt %, preferably 1 to 5 wt % of the total amount of the peptides and the free amino acids in the hydrolysate. At less than 1 wt %, desired in vivo absorbability is lowered and the expression of the functions is insufficient.

In the casein hydolysate of the present invention, Xaa in the dipeptides having the sequence Xaa-Pro and in the tripeptides having the sequence Xaa-Pro-Pro, may be any amino acid.

The casein hydrolysate of the present invention may preferably contain Ile-Pro, Glu-Pro, Arg-Pro, Gln-Pro, Met-Pro, and Tyr-Pro as the dipeptides having the sequence Xaa-Pro, and Ser-Pro-Pro, Ile-Pro-Pro, and Val-Pro-Pro as the tripeptides having the sequence Xaa-Pro-Pro.

The casein hydrolysate of the present invention, when contains such dipeptides and tripeptides, effectively exhibits in particular ACE inhibitory activity and hypotensive effect.

The casein hydrolysate of the present invention contains free amino acids in addition to the peptides. The content of the free amino acids is usually 35 to 50 wt %, preferably 40 to 45 wt % of the total amount of the peptides and the free amino acids in the hydrolysate.

The casein hydrolysate of the present invention may optionally contain, in addition to the peptides and the free amino acids, for example, lipid, ash, carbohydrate, dietary fibers, and water, which are usually contained in commercially available animal milk casein, in an amount of about 10 to 20 wt %. Some or all of these ingredients may be removed as desired.

The casein hydrolysate of the present invention may be prepared, for example, by the method of the present invention including the step of (A) hydrolyzing animal milk casein to have an average chain length of not longer than 2.1 with a group of enzymes capable of digesting animal milk casein into a hydrolysate having an average chain length of not longer than 2.1 in terms of the number of amino acid residues.

The animal milk casein is a protein having a high Pro content and confirmed safety for use in food and the like, and may be, for example, casein from cow's milk, horse's milk, goat's milk, and sheep's milk, with cow's milk casein being particularly preferred.

The casein concentration in hydrolyzing animal milk casein is not particularly limited, and may preferably be 3 to 19 wt % for efficient production of the hydrolysate of the present invention.

The group of enzymes used in the method of the present invention may be any group of enzymes wherein enzymes capable of digesting animal milk casein into a hydrolysate having an average chain length of not longer than 2.1 in terms of the number of amino acid residues are suitably selected and combined. For example, a group of enzymes (X) containing peptidases capable of cleaving the peptide bond Pro-Xaa in the carboxyl terminal of Xaa-Pro-Xaa or Xaa-Pro-Pro-Xaa, may preferably be used.

The group of enzymes (X) may preferably contain serine proteinases having serine at the active center, or metalloproteinases having a metal at the active center. The metalloproteinases may be neutral protease I, neutral protease II, or leucine amino peptidase. With at least one of these metalloproteinases, the objective hydrolysate may be obtained efficiently in a short time, and even in a one-step reaction, thus being preferred. The peptidases capable of cleaving the peptide bond Pro-Xaa may preferably be enzymes having isoelectric points in the acid region.

The group of enzymes or the group of enzymes (X) may be, for example, a group of extracellular enzymes derived from koji mold such as *Aspergillus oryzae*. Such a group of extracellular enzymes maybe those obtained by culturing cell body in an appropriate medium, and water-extracting the enzymes produced extracellularly. A group of extracellular enzymes derived from *Aspergillus oryzae* having isoelectric points in the acid region are particularly preferred.

The group of extracellular enzymes derived from *Aspergillus oryzae* may be a commercial product, such as SUMIZYME FP, LP, or MP (all registered trademarks, manufactured by SHIN NIHON CHEMICAL CO., LTD.), UMAMIZYME (registered trademark, manufactured by AMANO ENZYME, INC.), Sternzyme B11024 and PRO-HIDROXY AMPL (both trade names, manufactured by HIGUCHI INC.), ORIENTASE ONS (registered trademark, manufactured by HANKYU BIOINDUSTRY CO.), and DENAZYME AP (registered trademark, manufactured by NAGASE SEIKAGAKU), with SUMIZYME FP (registered trademark, manufactured by SHIN NIHON CHEMICAL CO., LTD.) being particularly preferred.

Such commercially available enzymes usually have specific optimum conditions. The conditions, such as the amount of enzymes used and the reaction time, may suitably be adjusted depending on the group of enzymes used so that the casein hydrolysate of the present invention may be obtained.

For the hydrolysis, the group of enzymes may be, for example, added to an aqueous solution of animal milk casein at a group of enzymes/animal milk casein ratio of not lower than 1/1000, preferably 1/10 to 1/1000, more preferably 1/10 to 1/100, most preferably 1/10 to 1/40, by weight.

The reaction conditions may suitably be selected depending on the group of enzymes used so that the objective casein hydrolysate is obtained. The reaction may usually be effected at 25 to 60° C., preferably 45 to 55° C., at pH 3 to 10, preferably 5 to 9, more preferably 5 to 8. The enzyme reaction time is usually 2 to 48 hours, preferably 7 to 15 hours.

The enzyme reaction may be terminated by inactivating the enzymes. Usually, the enzymes are inactivated at 60 to 110° C. to terminate the reaction.

After the termination of the enzyme reaction, the resulting precipitate may preferably be removed by centrifugation or through various filters, as desired.

Further, the obtained hydrolysate may be subjected to removal of peptides having bitter taste or odor, which may be effected using activated carbon, a hydrophobic resin, or the like. For example, 1 to 20 wt % of activated carbon with respect to the amount of casein used may be added to the hydrolysate, and reacted for 1 to 10 hours to remove such bitter and odorous components. The activated carbon used may be removed by a conventional method, such as centrifugation or membrane filtration.

The reaction liquid containing the casein hydrolysate obtained by step (A) may be added as it is to liquid products such as beverages. For improving the versatility of the casein hydrolysate of the present invention, the reaction liquid may preferably be concentrated and dried into powders.

Such powders may be used as various functional food, additives therefor, medicine, and an active ingredient thereof. The powders may optionally be mixed with various auxiliary additives for improving the nutritional balance or flavor. Examples of such auxiliary additives may include various carbohydrates, lipids, vitamins, minerals, sweeteners, flavoring agents, pigments, and texture improvers.

The powders containing the casein hydrolysate of the present invention may be used by adding to, for example, beverages, yogurt, liquid food, jelly, candies, retort food, tablet candies, cookies, sponge cakes, bread, biscuits, chocolate, and the like, or by formulating into capsules, tablets, and the like.

Since the casein hydrolysate of the present invention may be used in the above mentioned manner, the present hydrolysate may effectively be used in the manufacture of functional food such as various isotonic drinks, general beverages, general foods, dietary supplements, nutritional functional food, having health benefit incorporated therein, or in the manufacture of medicine.

The casein hydrolysate of the present invention has been confirmed to have ACE inhibitory activity and hypotensive effect in the Examples to be discussed later, so that the present hydrolysate may be used, for example, as an agent for the manufacture of functional food having such activity and effect, or as an agent for the manufacture of medicine.

When the casein hydrolysate of the present invention is used as an agent having ACE inhibitory activity and hypotensive effect, a preferred dose of the agent for oral administration to human is usually such as to allow ingestion of 0.1 to 100 mg/kg, preferably 1 to 20 mg/kg of the peptides and the free amino acids in the casein hydrolysate per administration. Thus the amount of the casein hydrolysate of the present invention or the agent having ACE inhibitory activity and hypotensive effect, when used by adding in various beverages, food, or medicine, may suitably be selected in view of the above dose.

According to the method of the present invention, by hydrolyzing animal milk casein in a one-step reaction with a group of enzymes containing the group of enzymes (X) mentioned above, Xaa-Pro-Pro contained in the animal milk casein, in particular Ile-Pro-Pro and/or Val-Pro-Pro, of which various functions including hypotensive effect and anti-stress effect have been confirmed, may be obtained at a higher yield closer to the theoretical recovery, such as not lower than 60%, preferably not lower than 70%, compared to the conventional methods. Thus this method is not only a method for preparing a casein hydrolysate of the present invention, but also an effective method for producing digested products containing a considerable amount of objective Xaa-Pro-Pro, or purified products thereof, from animal milk casein or food protein having a high Xaa-Pro-Pro content.

EXAMPLES

The present invention will now be explained in more detail with reference to Examples, Analysis Example, and Comparative Examples, which are illustrative only and do not intend to limit the present invention.

Example 1 and Comparative Examples 1 to 8

1 g of casein derived from cow's milk (manufactured by NIPPON NZMP) was added to 99 g of distilled water at about 80° C. and thoroughly mixed. A 1N sodium hydroxide (manufactured by WAKO PURE CHEMICAL INDUSTRIES, LTD.) solution was added to the mixture to adjust the pH to 7.0. The temperature was adjusted to 20° C., to prepare a substrate solution.

To the substrate solution thus obtained, each of the various enzymes shown in Table 1 was added so that the enzyme/casein ratio was 1/25 by weight. The mixture was reacted at 50° C. for 14 hours, and then subjected to autoclaving at 110° C. for 10 minutes to inactivate the enzymes, to thereby obtain a solution of enzymatic digestion products of casein. The obtained solution of enzymatic digestion products was spray-dried, to prepare powders.

The powders thus obtained were subjected to analysis of ingredients. Protein was determined by Kjeldahl method, and amino acids with an amino acid analyzer. The amount obtained by subtracting the amount of amino acids from the amount of protein was taken as the amount of peptides. Further, the amount of lipids was determined by the method with acid hydrolysis, ash by direct ignition, and water by the air oven method. The amount of each ingredient was subtracted from 100%, of which balance was taken as the amount of carbohydrate. As a result, the powders were determined to contain 35.8 wt % amino acids, 45.7 wt % peptides, 6.6 wt % water, 0.2 wt % lipid, 4.1 wt % ash, and 7.6 wt % carbohydrate.

<Measurement of Average Chain Length>

The average chain length of the amino acids and the peptides contained in the obtained powders was determined by measuring the number of moles using an OPA reagent, which reacts with amino groups of the free amino acids and the peptides in the powders, similarly measuring the number of moles of a casein acid hydrolysate, and evaluating the ratio of these two. The results are shown in Table 1.

40 mg of o-phthalaldehyde (guaranteed reagent for fluorescence analysis, manufactured by NACALAI TESQUE, INC.) was dissolved in 1 ml of methanol, and 100 µl of β-mercaptoethanol was added. The o-phthalaldehyde solution was diluted to 25 ml with 25 ml of a 100 mM sodium tetraborate solution previously mixed with 2.5 ml of 20% dodecyl sodium sulfate, and further to 50 ml with distilled water, to prepare an OPA reagent.

Each powder sample of 1% casein enzyme hydrolysate obtained by reaction with each enzyme (Table 1) was dissolved in an appropriate solvent at an appropriate concentration, and centrifuged at 15000 rpm for 10 minutes. 50 µl of the supernatant was taken out. Then 1 ml of the OPA reagent prepared above was added, thoroughly stirred, and left at a room temperature for 5 minutes. The absorbance at 340 nm was measured using an absorptiometer (trade name Ubest-35, manufactured by JASCO CORPORATION).

A 1% casein acid hydrolysate was prepared, properly diluted, and subjected to the same measurement to obtain a calibration curve, from which the relationship between absorbance and molar concentration was determined. The average chain length was calculated in accordance with the following formula:

Average chain length=(molar concentration of 1% casein acid hydrolysate)/(molar concentration of each sample 1% casein enzyme hydrolysate)

TABLE 1

| | Origin of enzyme | Commercial enzyme | Average chain length |
|---|---|---|---|
| Example 1 | Aspergillus oryzae | SUMIZYME FP [1] | 1.4 |
| Comp. Ex. 1 | Pig spleen | Trypsin [2] | 6.0 |
| Comp. Ex. 2 | Bacillus subtilis | SUMIZYME CP [3] | 4.1 |
| Comp. Ex. 3 | Bacillus stearothermophilus | PROTEASE S [4] | 4.5 |
| Comp. Ex. 4 | Carica papaya | Purified papain [5] | 7.9 |
| Comp. Ex. 5 | Bacillus thermoproteolyticus | Thermoase [6] | 4.6 |
| Comp. Ex. 6 | Rizopus niveus | NEURASE F3G [7] | 4.9 |
| Comp. Ex. 7 | Rizopus delemar | SUMIZYME RP [8] | 4.0 |
| Comp. Ex. 8 | Pineapple cannery | BROMELAIN [9] | 5.5 |

[1], [3], [8], [9] manufactured by SHIN NIHON CHEMICAL CO., LTD.;
[2] manufactured by HIGUCHI, INC.;
[4] manufactured by AMANO ENZYME, INC.;
[5] manufactured by NAGASE & CO., LTD.;
[6] manufactured by DAIWA KASEI K.K.;
[7] manufactured by NOVOZYME JAPAN <Measurement of Amino Acids Constituting Peptides>

The powders prepared in Example 1 were dissolved in a suitable amount of distilled water, and analyzed using an automatic peptide analyzer (trade name PPSQ-10, manufactured by SHIMADZU CORPORATION) to determine the amino acid residues from the N-terminal in the powders. The results are shown in Table 2. Incidentally, the automatic peptide analyzer does not detect free amino acids.

The total amount of the fifth amino acid residues was 120 pmol, and the total amount of the sixth amino acid residues was 100 pmol. From these results, it was found that most of the peptides contained in the powders were dipeptides and tripeptides. It was also found that the percentage of peptides having Pro at the second residue was 49.5%, which was remarkably high, and the percentage of peptides having Pro at the third residue was 29.8%, which was also high.

Thus it is expected that the powders contain a considerable amount of Xaa-Pro and Xaa-Pro-Pro, which are highly resistant against the enzymatic digestion with in vivo proteases, so that these peptides are optimal for use as functional peptides.

TABLE 2

| Amino acid | 1st residue (pmol) | 2nd residue (pmol) | 3rd residue (pmol) | 4th residue (pmol) | Content in casein (wt %) |
|---|---|---|---|---|---|
| Asp | 82 | 304 | 115 | 63 | 6.6 |
| Glu | 139 | 127 | 89 | 121 | 20.5 |
| Asn | 55 | 49 | 46 | 91 | included in Asp |
| Gln | 80 | 97 | 104 | 80 | included in Glu |
| Ser | 105 | 36 | 27 | 16 | 5.23 |
| Thr | 31 | 16 | 25 | 18 | 4.2 |
| His | 28 | 94 | 58 | 0 | 2.6 |
| Gly | 256 | 38 | 33 | 16 | 1.9 |
| Ala | 323 | 101 | 58 | 30 | 2.8 |
| Tyr | 725 | 114 | 52 | 28 | 5.4 |
| Arg | 13 | 7 | 6 | 8 | 3.6 |
| Met | 182 | 43 | 36 | 10 | 2.5 |
| Val | 869 | 127 | 196 | 64 | 6.1 |
| Pro | 42 | 1371 | 431 | 186 | 10.1 |
| Trp | 94 | 46 | 26 | 6 | 1.3 |
| Phe | 800 | 88 | 60 | 28 | 4.6 |
| Lys | 81 | 33 | 57 | 19 | 7.5 |
| Ile | 350 | 37 | 17 | 10 | 5.1 |
| Leu | 400 | 39 | 50 | 10 | 9.4 |
| Total | 4317 | 2767 | 1447 | 387 | 100.0 |

<Evaluation of Absorbability and Digestion Resistance of Xaa-Pro and Xaa-Pro-Pro in Living Organism>

In order to evaluate the absorbability and digestion resistance in living organism of the peptides having the sequence Xaa-Pro or Xaa-Pro-Pro contained in the powders of the casein enzyme hydrolysate prepared in Example 1 and shown in Table 1, the absorption of the peptides into blood after oral administration was tested in rats as follows.

To two six-week-old SD (Sprague Dawley) rats, 500 mg/animal each of Val-Pro-Pro as an example of Xaa-Pro-Pro and Gly-Gly as a dipeptide having no Pro were administered orally. Blood samples were taken from the portal vein at intervals, and the absorption of each peptide into blood was determined. The results are shown in FIG. 1.

Figure 1:
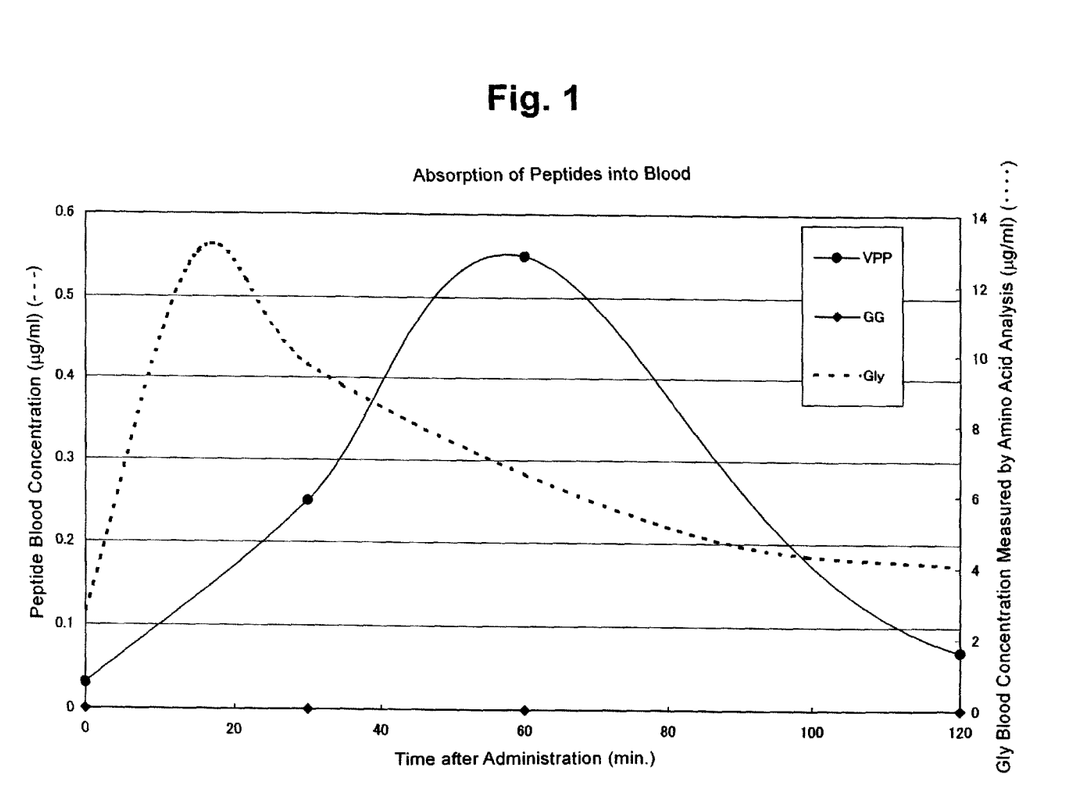
FIG. 1 is a graph showing the results of evaluation of in vivo absorbability and digestion resistance of Xaa-Pro and Xaa-Pro-Pro performed in Example 1.

From FIG. 1, it was confirmed that Gly-Gly was easily digested in vivo, so that Gly was detected, while Val-Pro-Pro was absorbed into blood relatively stably. From these results, it is expected that the dipeptides and tripeptides having the sequences Xaa-Pro and Xaa-Pro-Pro, respectively, exhibit high absorbability and digestion resistance in living organism.

<Evaluation of Hypotensive Effect>

Each of the casein hydrolysate powders prepared in Example and Comparative Examples shown in Table 1 were administered orally to five 27-week-old spontaneously hypertensive rats (SHR) (male) at a dose of 32 mg/kg body weight. Blood pressure was measured before the administration and 5 hours after the administration by tail-cuff method with Tail-cuff PB-98 (manufacture by SOFTRON) to evaluate the change in blood pressure. As a control, casein was administered instead of the powders, and the same evaluation was made. Before the measurement of blood pressure, rats were warmed in a preheat box (manufactured by CSI JAPAN) at 45° C. for 8 minutes. The results are shown in Table 3.

From Table 3, it is found that no change in blood pressure was observed with casein as a control, while the hypotensive effect was observed with the administration of the powders of Example 1. On the other hand, no change in blood pressure was observed with any of the powders of the Comparative Examples. It is thus demonstrated that the casein hydrolysate of Example 1 containing a particular amount of Xaa-Pro and Xaa-Pro-Pro and having an average chain length of not longer than 2.1 had excellent hypotensive effect.

Figure 2:
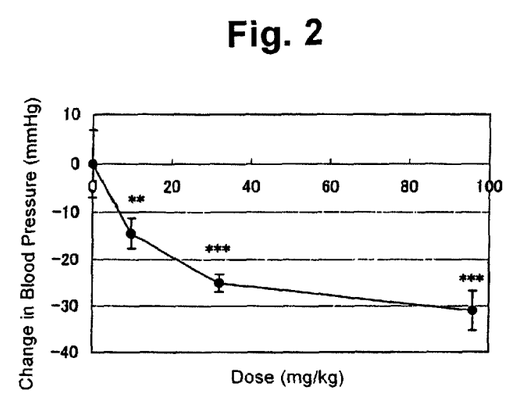
FIG. 2 is a graph showing the results of experiment for determining dose-dependent hypotensive effect of the casein hydrolysate powders prepared in Example 1.

Further, in accordance with the above method, a dose-dependent hypotensive effect was tested using the casein hydrolysate powders prepared in Example 1. The results are shown in Table 4 and FIG. 2.

<Evaluation of ACE Inhibitory Activity>

ACE derived from bovine lung (manufactured by WAKO PURE CHEMICAL INDUSTRIES, LTD.) was dissolved in a 0.1M borate buffer at pH 8.3 in an amount of 0.1 U, to obtain an ACE solution. 80 μl of a diluted enzyme hydrolysate solution prepared by diluting powders of each enzyme hydrolysate shown in Table 1 by 50-fold with distilled water, 200 μl of a 5 mM hippuryl-histidyl-leucine solution (manufactured by SIGMA), and 20 μl of the ACE solution prepared above were introduced into a tube, and reacted at 37° C. for 30 minutes. Subsequently, the reaction was terminated by adding 250 μl of 1N hydrochloric acid. 1.7 ml of ethyl acetate was then added, and stirred. 1.4 ml of the ethyl acetate layer was taken, placed in another tube, and evaporated at 120° C. for about 60 minutes to obtain a dried product. The dried product was dissolved in 1 ml of distilled water, and the absorbance at 228 nm of hippuric acid extracted with ethyl acetate was measured. As controls, absorbance was measured of a solution without the diluted enzyme hydrolysate solution and a solution without the diluted enzyme hydrolysate solution and the ACE solution. From the obtained absorbance, ACE inhibitory activity was calculated in accordance with the following formula. The results are shown in Table 3.

ACE inhibitory activity (%) = [(A−B)/A] × 100

A: (Absorbance of solution without diluted enzyme hydrolysate solution but with ACE solution) − (Absorbance of solution without diluted enzyme hydrolysate solution and ACE solution)

B: (Absorbance of solution with diluted enzyme hydrolysate solution and ACE solution) − (Absorbance of solution with diluted enzyme hydrolysate solution but without ACE solution)

TABLE 3

| Enzyme hydrolysate | ACE inhibitory activity (%/μg) | Blood pressure drop (average ± SD) |
|---|---|---|
| Example 1 | 4.1 | −25.0 ± 4.3 *** |
| Comp. Ex. 1 | 0.8 | −4.3 ± 5.3 |
| Comp. Ex. 2 | 1.2 | — |
| Comp. Ex. 3 | 1.4 | −3.7 ± 6.4 |
| Comp. Ex. 4 | 1.0 | 2.8 ± 5.2 |
| Comp. Ex. 5 | 1.1 | — |
| Comp. Ex. 6 | 0.9 | 2.9 ± 5.4 |
| Comp. Ex. 7 | 0.7 | −5.1 ± 7.0 |
| Comp. Ex. 8 | 1.1 | −4.6 ± 6.9 |
| Control | — | −2.5 ± 7.5 |

TABLE 4

| Dose of powders (mg/kg) | Change in blood pressure (mmHg) | Standard Deviation |
|---|---|---|
| 96 | −31 | 4.3 |
| 32 | −25 | 1.9 |
| 9.6 | −14.4 | 3.2 |
| 0 | 0 | 6.9 |

<Determination of Peptides in Enzyme Hydrolysate>

The powders of the enzyme hydrolysate of Example 1 shown in Table 1 were dissolved in distilled water at a concentration of 10 mg/ml. On the other hand, 25 μg/ml, 50 μg/ml and 100 μg/ml solutions of each chemically synthesized standard peptide having the sequence shown in Table 5 were prepared. These solutions were analyzed by LC/MS under the conditions below. Among the peaks indicated in the analysis of the powder solution, peaks corresponding to the molecular weights and the retention times identical with those of standard peptides were identified as representing the same sequences as the standard peptides. The peaks of the powder solution were compared to those of the standard peptides, to determine the content of each peptide shown in Table 4 in the powder solution. The results are shown in Table 5.

It was found that the amount of the peptides and the free amino acids in the solution prepared by dissolving the powders with distilled water was 8.15 mg/ml, the amount of peptides was 4.57 mg/ml, and the amount of Xaa-Pro in the peptides was 514.5 μg, so that the percentage of Xaa-Pro with respect to the total amount of the peptides and the free amino acids in the powders was 6.3 wt %. Further, the amount of Xaa-Pro-Pro in the peptides was 116.5 μg, so that the percentage of Xaa-Pro-Pro with respect to the total amount of the peptides and the free amino acids in the powders was 1.4 wt %.

<Apparatus Used>

High performance liquid chromatograph-mass spectrometer: LCMS-2010; System controller: SCL-10Advp; Automatic injector: SIL-10Advp; Solvent delivery pump: LC-10Advpx2; Column oven: CTO-10Avp; Photodiode array detector: SPD-M10AVP, Online degasser: DGU-14A (all trade names, manufactured by SHIMADZU CORPORATION); Column: Develosil C30-UG-3 (2.0 mmI.D.×150 mmL) (manufactured by NOMURA CHEMICAL CO., LTD.)

<Conditions for Measurement>

Mobile phase A: aqueous solution of 0.1 wt % formic acid; Mobile phase B: 100% acetonitrile solution; Time program: 0% B (0 minute) — 7.5% B (30 minutes) — 80% B (30.01 minutes) — 100% B (35 minutes) — 0% B (35.1 minutes) — STOP (45 minutes); Amount of sample for injection: 5 μl; Column temperature: 50° C.; Detection wavelength: 200 to 300 nm; Ionization mode: ESI (+); Atomized gas flow rate: 4.5 L/min; Applied voltage: +4.5 kV; CDL temperature: 250° C.; Block heater temperature: 200° C.; CDL voltage: 0.0 V; Q-array voltage: SCAN; Analysis mode: SIM measurement; Analyzed range: EP(m/z=245.2), IP(m/z=229.3), MP(m/z=247.3), QP(m/z=244.2), RP(m/z=272.3), SPP(m/z=300.3), VPP(m/z=312.1), IPP(m/z=326.1); Intake time: 0.5 sec/Ch.

TABLE 5

| Peptide sequence | Concentration in 10 mg/ml powders (μg/ml) |
|---|---|
| Ile-Pro | 16.0 |
| Glu-Pro | 7.1 |
| Arg-Pro | 10.3 |
| Gln-Pro | 34.5 |
| Met-Pro | 18.4 |
| Tyr-Pro | 128.9 |
| Other Xaa-Pro | 299.4 |
| Ser-Pro-Pro | 2.9 |
| Val-Pro-Pro | 29.5 |
| Ile-Pro-Pro | 28.1 |
| Phe-Pro-Pro | 27.2 |
| Other Xaa-Pro-Pro | 28.8 |

Analysis Example 1

<Identification of Enzymes>

Among the extracellular enzymes derived from *Aspergillus oryzae* used in Example 1, enzymes necessary for obtaining the casein hydrolysate of the present invention were analyzed in the following method. Incidentally, all the following operations were performed at 4° C. unless otherwise specified. The reagents used were all guaranteed reagents manufactured by WAKO PURE CHEMICAL INDUSTRIES, LTD. unless otherwise specified.

<Impact of Various Inhibitory Agents on Enzymes>

2000 mg of SUMIZYME FP (registered trademark, manufactured by SHIN NIHON CHEMICAL CO., LTD.) was dissolved in 10 ml of a 50 mM phosphate buffer at pH 7.2, and the insoluble was removed through a cellulose acetate membrane (DISMIC-25cs, pore diameter 0.45 μm, manufactured by ADVANTEC), to obtain a crude enzyme solution.

This crude enzyme solution was reacted with 1% casein in the same way as in Example 1. When a metalloprotease inhibitor, EDTA (ethylenediaminetetraacetic acid), or a serine protease inhibitor, PMSF (phenyl methane sulfonyl fluoride) was added to the reaction system, the average chain length was longer, and the objective hydrolysate could not be obtained. This suggests that the metalloprotease or serine protease plays an important role in the production of the casein hydrolysate of the present invention.

(Isolation with Ion Exchange Resin)

20 ml of an anion exchange resin, DEAE sephacel (manufactured by AMERSHAM BIOSCIENCES K.K.) was activated, equilibrated with a 50 mM phosphate buffer at pH 7.2, and packed in a glass column of 1.5 cm diameter×12 cm. While all the effluent was collected as non-adsorbed sample, the crude enzyme solution was subjected to adsorption at a flow rate of 1.0 ml/min. Then the column was thoroughly washed with a 50 mM phosphate buffer at pH 7.2 in an amount 10 times the volume of the gel, and eluted with 200 ml of a 50 mM phosphate buffer at pH 7.2 containing a linear gradient of NaCl (0 to 600 mM). The eluate was fractionated into 100 fractions of 5 ml each. The absorbance at 280 nm, the proteinase activity, and the ACE inhibitory activity were measured for each fraction.

(Measurement of Proteinase Activity)

25 mg of a fluorescent material, (fluorescein isothiocyanate)-labeled casein (FITC-casein, manufactured by SIGMA) was dissolved in 5 ml of a 50 mM phosphate buffer at pH 7.2 to prepare a substrate solution. 10 µl of each fraction was mixed with 20 µl of the substrate solution, and reacted at 55° C. for 10 minutes. The reaction was terminated by adding 120 µl of a 5% trichloroacetate solution, and the resulting reaction liquid was centrifuged at 1500 rpm. 60 µl of the supernatant was taken, mixed with 3 ml of a 0.5 M trishydrochloride at pH 8.5, and subjected to measurement using a fluorometer (F-1300, manufactured by HITACHI, LTD.) to determine the excitation wavelength at 485 nm, and the fluorescence wavelength at 525 nm.

Figure 3:
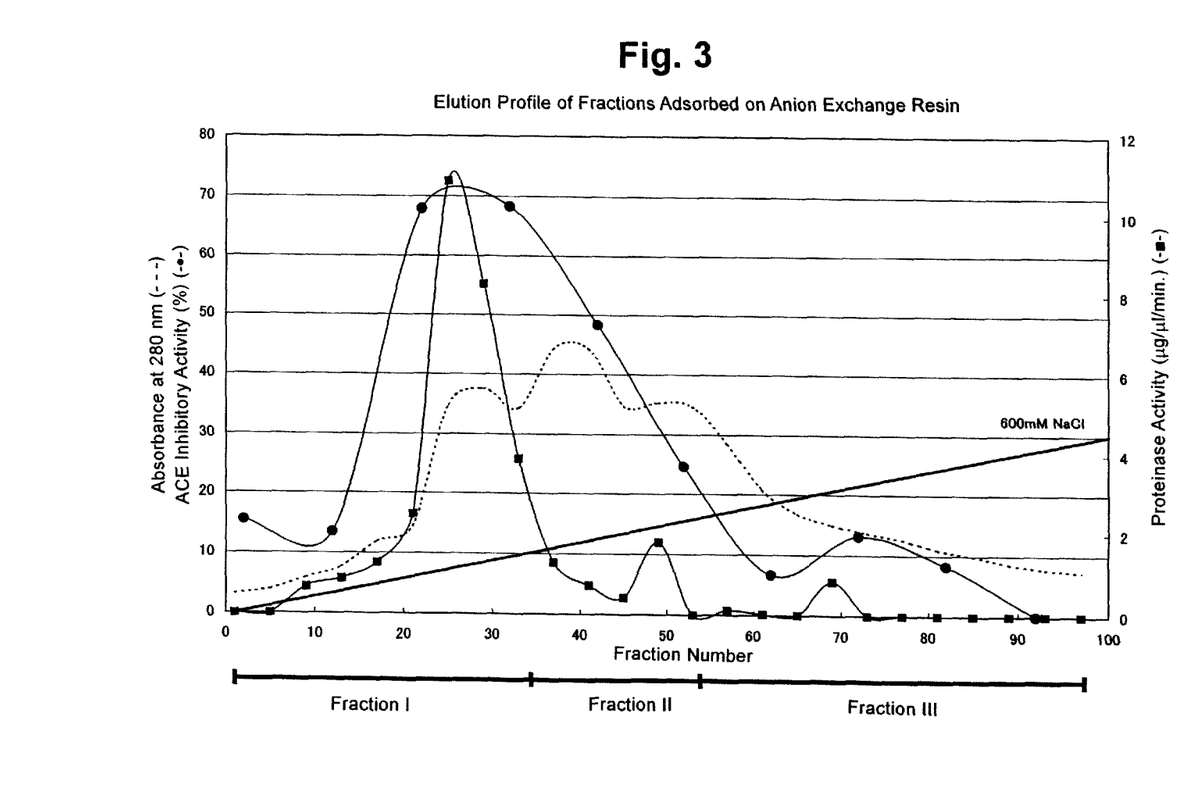
FIG. 3 is a graph showing the relationship between the elution pattern of bound protein with a linear gradient of 0 to 0.6 M NaCl and the proteolytic activity in Analysis Example 1.

From the results of the measurement of absorbance at 280 nm of each DEAE sephacel eluate fraction, it was confirmed that about 73% of the protein was adsorbed on the anion ion exchange resin. FIG. 3 shows the elution pattern of the bound protein with a linear gradient of 0 to 0.6 M NaCl and the proteolytic activity.

Fractions 21 to 60 contained a particularly large amount of proteins eluted therein. Further, the eluted enzyme solution of each fraction was evaluated for the activity to generate ACE inhibitory components in hydrolyzing casein. As a result, fractions 20 to 60 were mainly confirmed to have the activity to generate ACE inhibitory components.

On the other hand, the proteinase activity measured with the FITC-casein as the substrate was observed mainly in fractions 19 to 27 (at 0.1 M to 0.2 M NaCl), which indicates that the proteinase activity has an important function in generation of ACE inhibitory components. From these results, it was found that the proteinase activity plays an important role in the enzymatic activity for purifying the ACE inhibitory components from casein.

(Identification of Proteinases Contained)

From the DEAE sephacel eluted fractions, fractions 21 to 35 having the proteinase activity were collected, and dialyzed against 5 liters of a 5 mM phosphate buffer at pH 7.2. Sephacryl S-300 HR (manufactured by AMERSHAM BIOSCIENCES K.K.) was suspended in a 50 mM phosphate buffer at pH 7.2 containing 200 mM NaCl, fully degassed, and packed in a glass column of 18 cm in diameter×100 cm. This column was fully equilibrated with a 50 mM phosphate buffer at pH 7.2 containing 200 mM NaCl at a constant flow rate of 2 ml/min. The dialyzed sample was applied to this column, and 100 fractions of 10 ml each were recovered. The absorbance at 280 nm and the proteinase activity using FITC-casein as a substrate were measured for each fraction.

(Polyacrylamide Gel Electrophoresis)

10 µl of each fraction was taken, mixed with 10 µl of a sample buffer composed of a 0.125 M Tris buffer at pH 6.8, 3% SDS, 5% β-mercaptoethanol, 10% glycerol, and 0.01% bromophenol blue, heated at 95° C. for 5 minutes, and cooled at a room temperature. The resulting sample was subjected to electrophoresis according to the Laemmli method (Nature, 227, 680 (1970)), using a mini-slab (manufactured by ATTO CORPORATION) and a polyacrylamide gel at a designated concentration under the conditions of 30 mA per gel. After the completion of the electrophoresis, the gel was soaked in a Coomassie Brilliant Blue stain solution composed of 0.25% Coomassie Brilliant Blue R-250, 50% methanol, and 7.5% acetic acid for 10 minutes, and infiltrated in a decolorant composed of 5% methanol and 7.5% acetic acid until the background was completely decolored. The molecular weight was figured by calculation from the mobility of each protein band, using molecular weight markers (manufactured by AMERSHAM BIOSCIENCES K.K.).

The fractions adsorbed on the anion exchange resin having the activity to generate ACE inhibitory components, were subjected to gel filtration through Sephacryl S-300 resin, and the activity was observed in fractions corresponding to the molecular weight of about 45 kDa. These fractions were analyzed by SDS-polyacrylamide gel electrophoresis in a 12.5% gel to observe a substantially single band at 44 kDa and 40 kDa. These bands were cut out, and subjected to analysis of the N-terminal sequences. It was revealed that the band at 44 kDa had a sequence that was highly homologous to a known neutral protease I of koji mold (*Aspergillus*), and the band at 40 kDa had a sequence that was highly homologous to a known neutral protease II of koji mold (*Aspergillus*).

From these results, it was determined that the proteinases adsorbed on the anion exchange resin that generated ACE inhibitory components for casein, contained at least two proteinases, neutral protease I and neutral protease II.

For further hydrolyzing the components generated by hydrolysis of casein with proteinases, peptidases, which act on peptides, were analyzed in the following method.

In order to identify the enzymes for producing peptides having higher contents of Xaa-Pro and Xaa-Pro-Pro, which are the characteristic feature of the present invention, various precursor peptides for Val-Pro-Pro were synthesized, and their processability into Val-Pro-Pro was evaluated.

(Purification of Enzymes for Processing Amino Terminals)

From the DEAE sephacel eluted fractions, fractions 21 to 37 having the activity to generate ACE inhibitory components were collected, and dialyzed against 5 liters of a 5 mM phosphate buffer at pH 7.2. Hydroxyapatite (manufactured by WAKO PURE CHEMICAL INDUSTRIES, LTD.) was suspended in a 5 mM phosphate buffer at pH 7.2, fully degassed, and packed in a plastic column of 1.5 cm in diameter×12 cm. This column was washed with a 5 mM phosphate buffer at pH 7.2 in an amount not less than 10 times the amount of the hydroxyapatite. The dialyzed fractions having the activity to generate ACE inhibitory components were applied to this hydroxyapatite column, and all the fractions passed through the column were collected.

(Measurement of Aminopeptidase Activity)

Aminopeptidase activity was measured by the following method. Synthesized peptide Val-Val-Val-Pro-Pro was dissolved in a 50 mM phosphate buffer at pH 7.2 at a concentration of 50 µg/ml to prepare a substrate solution. 45 µl of this substrate solution was mixed with 5 µl of the enzyme fraction, and reacted in an incubator at 55° C. for 30 minutes. The reaction was terminated by heating at 98° C. for 5 minutes. An appropriate amount of this reaction liquid was taken, and subjected to analysis in a high performance liquid chromatograph-mass spectrometer (manufactured by SHIMADZU CORPORATION) to evaluate the amount of Val-Pro-Pro generated.

The fractions adsorbed on the anion exchange resin having the activity to generate ACE inhibitory components were subjected to SDS-polyacrylamide gel electrophoresis in a 10% gel, and the band at 32 kDa was cut out. The major protein was extracted, and purified into a substantially single protein of 32 kDa. The sequence in the N-terminal of the protein was analyzed to reveal that the sequence up to the tenth residue from the N-terminal was homologous to the sequence of known leucine aminopeptidase of koji mold (*Aspergillus*). It was concluded that the fractions having the confirmed activity to generate ACE inhibitory components contained leucine aminopeptidase.

From these results, it is understood that the fractions adsorbed on the anion exchange resin having the activity to generate ACE inhibitory components contained at least leucine aminopeptidase having aminopeptidase activity, which played an important role in the activity to generate ACE inhibitory components.

(Measurement of Carboxyl Terminal Processability of Enzymes)

Synthesized peptide Val-Pro-Pro-Phe-Leu was dissolved in a 50 mM phosphate buffer at pH 7.2 at a concentration of 45 µg/ml to prepare a substrate solution. 50 µl of this substrate solution was mixed with 5 µl of each enzyme solution, and reacted in an incubator at 55° C. for 30 minutes. The reaction was terminated by heating at 98° C. for 5 minutes. An appropriate amount of this reaction liquid was taken, and subjected to analysis in a high performance liquid chromatograph-mass spectrometer (manufactured by SHIMADZU CORPORATION) to evaluate the concentration of Val-Pro-Pro generated.

The carboxyl terminal processability of each DEAE sephacel eluted fraction was evaluated to find that fractions 30 to 50 had enzymatic activity to convert Val-Pro-Pro-Phe-Leu to Val-Pro-Pro.

Example 2

(Confirmation of ACE Inhibitory Activity of Casein Hydrolysate by Purified Enzyme Combination)

From Analysis Example 1, it was confirmed that the activity to generate ACE inhibitory components of the fractions adsorbed on the anion exchange resin of the extracellular enzyme derived from *Aspergillus oryzae* (SUMIZYME FP (registered trademark, manufactured by SHIN NIHON CHEMICAL CO., LTD.)) included four enzymatic activities, i.e., the proteinase activities including those of at least neutral proteases I and II, the aminopeptidase activity including that of leucine aminopeptidase, and the activity to cleave the carboxyl terminal at immediately after proline.

From the adsorbed fractions (see FIG. 3), Fraction I having high proteinase activity (fractions 1 to 35 in FIG. 3), Fraction II having high activity to cleave the carboxyl terminal at immediately after proline (fractions 36 to 55 in FIG. 3), Fraction III thereafter (fractions 56 to 100 in FIG. 3), and non-adsorbed fractions having proteinase activity were provided.

Each Fraction was added, alone or in combination as shown in Table 6, to 1 ml of a 1% solution of casein derived from cow's milk, reacted at 55° C. for 13 hours to prepare a casein hydrolysate. After the completion of the reaction, each of the obtained casein hydrolysates was measured for the ACE inhibitory activity and the average chain length in accordance with the method described in Example 1. As a control, the crude enzyme solution in 1/10000 the amount subjected to the purification was subjected to the same measurements. The results are shown in Table 6.

TABLE 6

| Fractions Used | ACE inhibition (%) | Average chain length of digested products |
|---|---|---|
| Crude enzyme fractions | 79 | 1.8 |
| Non-adsorbed fractions | 45 | 3.7 |
| Fraction I | 46 | 2.3 |
| Fraction II | 27 | 2.75 |
| Fraction III | 0 | — |
| Non-adsorbed fractions + Fraction II | 70 | 2.1 |
| Fractions I + II | 56 | 1.8 |
| Non-adsorbed fractions + Fractions I + II | 77 | 1.7 |
| Non-adsorbed fractions + Fractions I + II + III | 78 | 1.6 |
| Non-adsorbed fractions + Fraction III | 52 | — |
| Fractions I + III | 40 | — |
| Fractions II + III | 12 | — |
| Non-adsorbed fractions + Fractions II + III | 68 | — |
| Fractions I + II + III | 43 | — |

From Table 6, it was found that components having strong ACE inhibitory activity were contained in the non-adsorbed fractions, the fractions having high proteinase activity, and up to the fractions having the activity to cleave the carboxyl terminal at immediately after proline. It was also found that the group of enzymes eluted at about 300 mM NaCl generated the ACE inhibitory components, so that Fraction III was unnecessary.

The average chain length of the casein hydrolysate obtained by hydrolysis with each fraction exhibiting the strong activity to generate ACE inhibitory components, was measured and compared. It was found that the average chain lengths for the non-adsorbed fractions, Fraction I, and Fraction II were over 2.1, but by combining these fractions, a casein hydrolysate having the average chain length of not longer than 2.1 was obtained.

Example 3

15 g of casein derived from cow's milk (manufactured by NIPPON NZMP) was added to 85 g of distilled water at about 80° C. and thoroughly mixed. 1N sodium hydroxide solution was added to the mixture to adjust the pH to 7.0. The temperature was adjusted to 20° C. to prepare a substrate solution.

Figure 4:
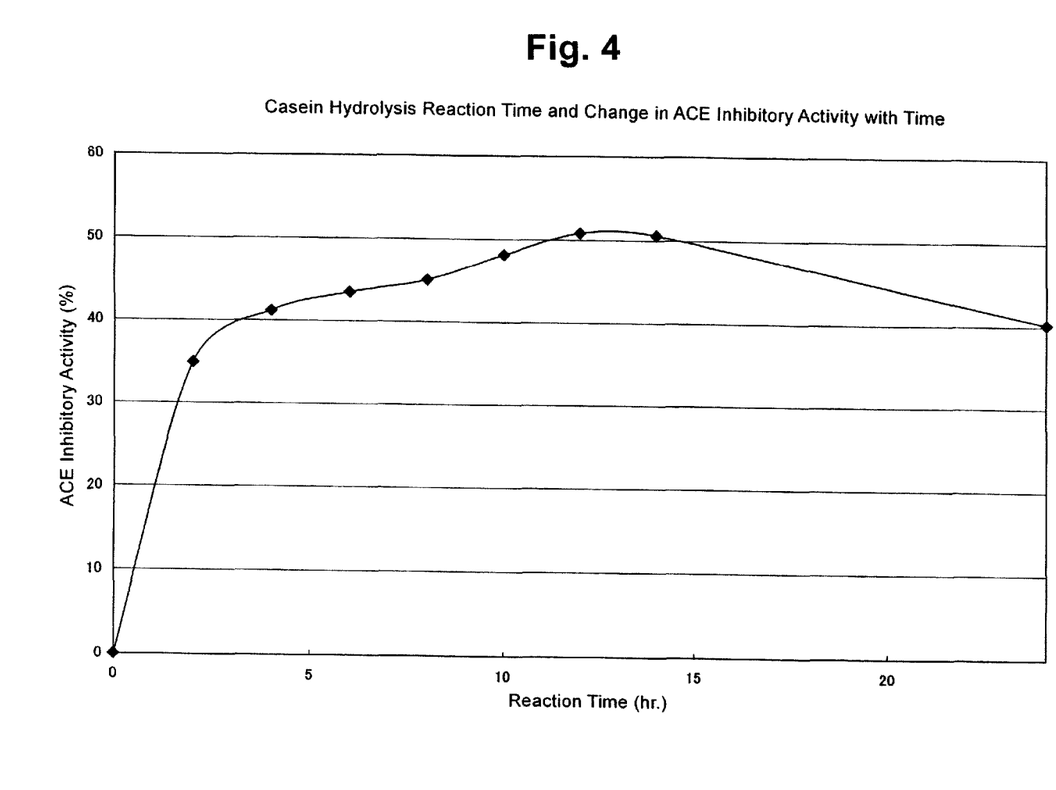
FIG. 4 is a graph showing the relationship between the digestion time of casein with the group of enzymes and the ACE inhibitory activity of the resulting casein hydrolysate in Example 3.
Figure 5:
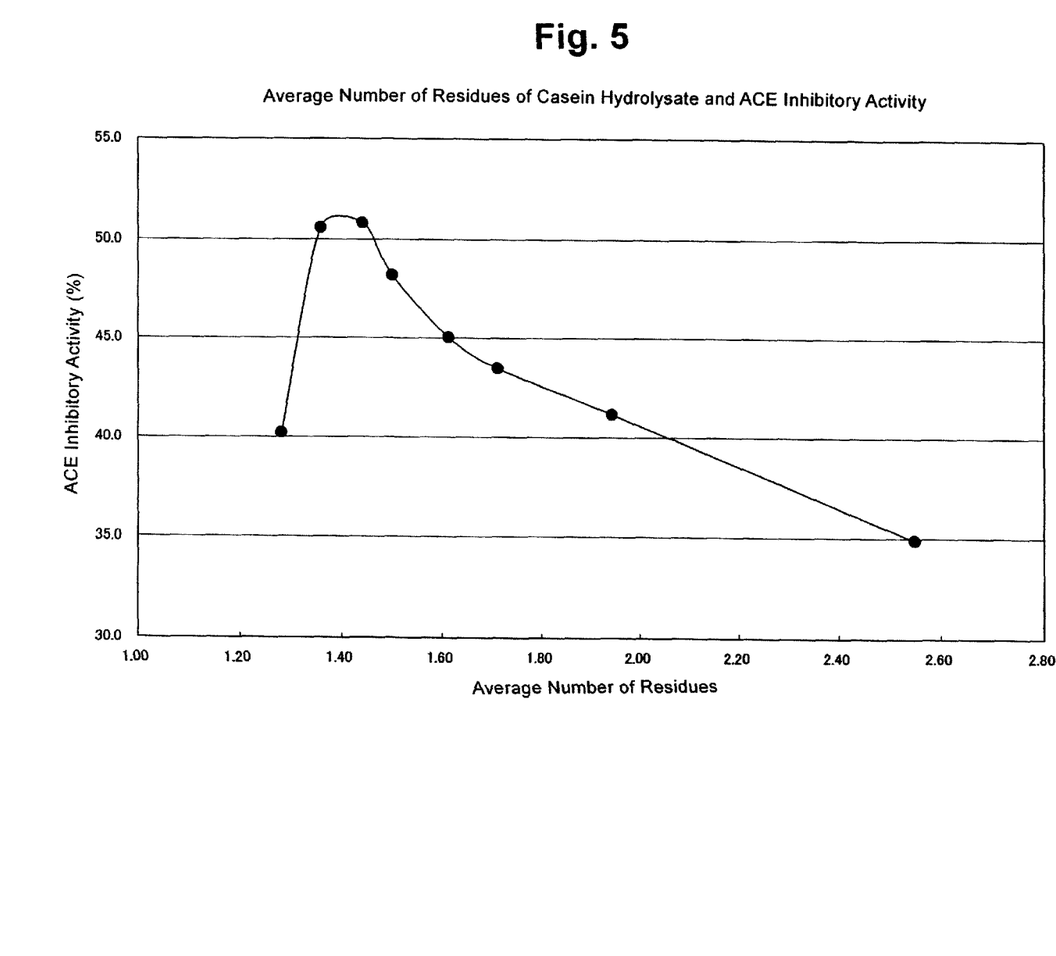
FIG. 5 is a graph showing the relationship between the average chain length and the ACE inhibitory activity of the casein hydrolysate obtained by hydrolysis of casein with the group of enzymes in Example 3.

To the substrate solution thus obtained, SUMIZYME FP (registered trademark, manufactured by SHIN NIHON CHEMICAL CO., LTD.), which is extracellular enzymes derived from *Aspergillus oryzae*, was added as the group of enzymes so that the enzyme/casein ratio was 1/25 by weight. The mixture was reacted at 50° C. for 20 hours, while the reaction liquid was sampled at intervals to evaluate the ACE inhibitory activity and the average chain length against time in the same way as in Example 1. The results are shown in FIGS. 4 and 5. The enzyme-digested solution taken after 12 hours of reaction, which exhibited the maximum ACE inhibitory activity, was spray-dried to obtain powders of peptide mixture.

From FIGS. 4 and 5, it was confirmed that the ACE inhibitory activity increased with the increase in reaction time, and decreased after 12 hours of reaction. It was also confirmed from the evaluation of the peptide amount that the ACE inhibitory activity increased at the average chain length of about 1.3 to 2.1.

What is claimed is:

1. A casein hydrolysate obtained by hydrolyzing animal milk casein with a group of enzymes, said hydrolysate comprising free amino acids and peptides, wherein the average amino acid chain length of said free amino acids and peptides in said hydrolysate is not longer than 2.1 amino acid residues, wherein said group of enzymes comprise peptidases capable of cleaving a peptide bond Pro-Xaa and leucine amino peptidases, and further comprises at least one of neutral protease I and neutral protease II, wherein said peptides comprise in vivo indigestible peptides consisting of dipeptides having a sequence Xaa-Pro and tripeptides having a sequence Xaa-Pro-Pro, wherein Xaa in Xaa-Pro and Xaa and Xaa-Pro-Pro is any amino acid present in animal milk casein, and wherein a content of said dipeptides having a sequence Xaa-Pro is not lower than 5 wt % of a total amount of the free amino acids and the peptides in the hydrolysate, and a content of said tripeptides having a sequence Xaa-Pro-Pro is not lower than 1 wt % of a total amount of the free amino acids and the peptides in the hydrolysate.

2. A composition comprising the casein hydrolysate of claim 1, wherein the composition is a food additive or a medicine.

3. The casein hydrolysate of claim 1, wherein said dipeptides having a sequence Xaa-Pro comprises Ile-Pro, Glu-Pro, Arg-Pro, Gln-Pro, Met-Pro, and Tyr-Pro, and said tripeptides having a sequence Xaa-Pro-Pro comprises Ser-Pro-Pro, Ile-Pro-Pro, and Val-Pro-Pro.

4. The casein hydrolysate of claim 1, wherein said peptidases capable of cleaving a peptide bond Pro-$X_{aa}$, leucine amino peptidases, neutral protease I, and neutral protease II are extracellular enzymes obtained from *Aspergillus oryzae*.

5. The casein hydrolysate of claim 1 wherein the animal is selected from the group consisting of a cow, a horse, a goat, and a sheep.

6. A method for preparing the casein hydrolysate of claim 1, the method comprising the steps of:
(A) hydrolyzing an animal milk casein with a group of enzymes capable of digesting the animal milk casein into a casein hydrolysate having an average amino acid chain length of not longer than 2.1 amino acid residues; and
(B) recovering the casein hydrolysate.

7. The method of claim 6, wherein said group of enzymes are extracellular enzymes obtained from *Aspergillus oryzae*.

8. The method of claim 6, wherein said hydrolyzing is performed in a one-step reaction with said group of enzymes.

9. The method of claim 6, wherein said group of enzymes comprises one or more peptidase capable of cleaving a Pro-Xaa peptide bond.

10. The method of claim 9, wherein said group of enzymes further comprises one or more metalloprotease and/or serine protease.

11. The method of claim 9, wherein said group of enzymes further comprises one or more of a neutral protease I, a neutral protease II, a leucine amino peptidases, and combinations thereof.

12. The method of claim 9, wherein said group of enzymes are extracellular enzymes obtained from *Aspergillus oryzae*.

13. The method of claim 9, wherein each of said one or more peptidases has an isoelectric point in an acid region.

14. The method of claim 6, wherein step (A) comprises providing an animal milk having by weight thereof said casein in an amount of 3 to 19% (w/w), and wherein by mass said group of enzymes and said animal milk casein are provided in an enzyme-to-casein ratio is not lower than 1/100 by mass.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Bos taurus

<400> SEQUENCE: 1

Val Val Val Pro Pro
1               5

<210> SEQ ID NO 2
<211> LENGTH: 5
<212> TYPE: PRT
<213> ORGANISM: Bos taurus

<400> SEQUENCE: 2

Val Pro Pro Phe Leu
1               5